(12) United States Patent
Blankenstein et al.

(10) Patent No.: US 10,363,559 B2
(45) Date of Patent: Jul. 30, 2019

(54) APPARATUS FOR THE SEPARATION OF PLASMA

(71) Applicant: Boehringer Ingelheim Microparts GmbH, Ingelheim am Rhein (DE)

(72) Inventors: Gert Blankenstein, Dortmund (DE); Holger Bartos, Dortmund (DE); Ralf-Peter Peters, Bergisch-Gladbach (DE); Christian Schoen, Dresden (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 217 days.

(21) Appl. No.: 15/358,185

(22) Filed: Nov. 22, 2016

(65) Prior Publication Data

US 2017/0165666 A1 Jun. 15, 2017

Related U.S. Application Data

(63) Continuation of application No. 12/867,335, filed as application No. PCT/EP2009/001383 on Feb. 26, 2009, now Pat. No. 9,539,572.

(30) Foreign Application Priority Data

Feb. 27, 2008 (DE) .................. 10 2008 011 339

(51) Int. Cl.
 *B01L 3/00* (2006.01)
 *B01D 29/01* (2006.01)
 (Continued)

(52) U.S. Cl.
 CPC ...... *B01L 3/502753* (2013.01); *B01D 29/014* (2013.01); *B01D 29/05* (2013.01);
 (Continued)

(58) Field of Classification Search
 CPC ..... B01L 2300/0681; B01L 2300/0864; B01L 2300/0654; B01L 2300/0825;
 (Continued)

(56) References Cited

U.S. PATENT DOCUMENTS

| 4,323,536 A | 4/1982 | Columbus |
| 5,733,449 A * | 3/1998 | Bowers .................. B01D 61/18 |
| | | 210/321.6 |

(Continued)

FOREIGN PATENT DOCUMENTS

| CA | 2359787 A1 | 4/2002 |
| DE | 19753849 A1 | 6/1999 |

(Continued)

OTHER PUBLICATIONS

International Search Report, Form PCT/ISA/210, for corresponding PCT/EP2009/001383; dated Dec. 10, 2009.

*Primary Examiner* — Pranav N Patel
(74) *Attorney, Agent, or Firm* — Matthew B. Dernier, Esq.

(57) ABSTRACT

The invention relates to an apparatus for separating blood and at the same time an apparatus (1) for absorbing blood (19) and separating components such as blood plasma, as a sample liquid (2), having a feed device (13) for receiving the blood (2), a separating device (15) for separating blood components as the sample liquid (2), a channel (3) which takes up the sample liquid (2) preferably exclusively by capillary forces and a fill device for filling the channel (3) with sample liquid (2) in an inlet or feed region (18) of the channel (3), wherein the separating device (15), particularly a membrane, is domed, more particularly convexly shaped and projects with the apex of the convex shape into the filling device in the direction of filling.

5 Claims, 12 Drawing Sheets

Figure 1:
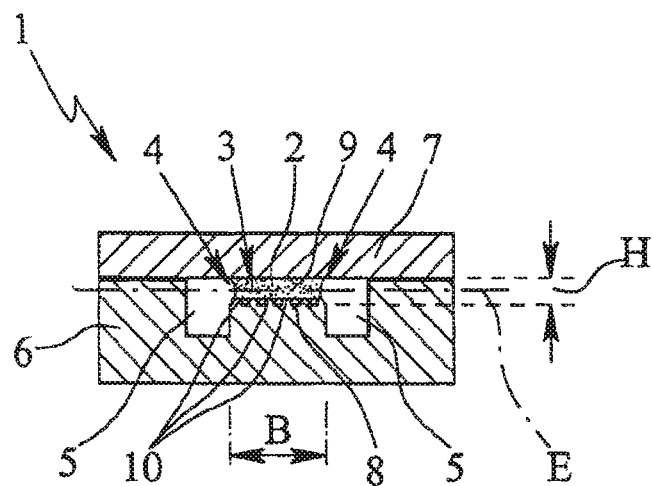

(51) Int. Cl.
 B01D 63/08 (2006.01)
 B01D 29/05 (2006.01)
 G01N 33/49 (2006.01)
 B01D 61/18 (2006.01)
(52) U.S. Cl.
 CPC ......... B01D 63/087 (2013.01); B01D 63/088 (2013.01); B01L 3/502715 (2013.01); G01N 33/491 (2013.01); B01D 61/18 (2013.01); B01D 63/08 (2013.01); B01D 2201/0415 (2013.01); B01D 2201/44 (2013.01); B01L 2300/0681 (2013.01); B01L 2300/0864 (2013.01); B01L 2400/0406 (2013.01)
(58) Field of Classification Search
 CPC ......... B01L 2300/089; B01L 2300/161; B01L 2400/0406; B01L 2400/084; B01L 2400/086; B01L 2400/088; B01L 3/502753; B01L 3/502715; B01L 2200/0621; B01L 2200/0684; B01D 2201/0415; B01D 2201/44; B01D 29/014; B01D 29/05; B01D 61/18; B01D 63/08; B01D 63/087; B01D 63/088
 See application file for complete search history.

(56) References Cited

U.S. PATENT DOCUMENTS

| | | | |
|---|---|---|---|
| 5,756,129 A | 5/1998 | Yoshii et al. | |
| 5,853,670 A * | 12/1998 | Bunce | B01L 3/5023 422/514 |
| 5,922,604 A | 7/1999 | Stapleton et al. | |
| 6,156,270 A * | 12/2000 | Buechler | B01J 19/0093 422/417 |
| 6,592,815 B1 | 7/2003 | Zimmer | |
| 7,931,868 B2 | 4/2011 | Blankenstein et al. | |
| 8,025,854 B2 | 9/2011 | Ohman et al. | |
| 2002/0192739 A1 | 12/2002 | Lemonnier | |
| 2003/0119177 A1 * | 6/2003 | Gruber | B01L 3/502761 435/287.2 |
| 2003/0175162 A1 * | 9/2003 | Anazawa | B01J 19/0093 422/537 |
| 2004/0077103 A1 | 4/2004 | Buechler | |
| 2004/0265171 A1 | 12/2004 | Pugia et al. | |
| 2005/0026346 A1 | 2/2005 | Blankenstein et al. | |
| 2005/0042766 A1 | 2/2005 | Ohman et al. | |
| 2005/0106756 A1 | 5/2005 | Blankenstein et al. | |
| 2005/0169778 A1 | 8/2005 | Blankenstein et al. | |
| 2006/0216195 A1 | 9/2006 | Blankenstein et al. | |
| 2006/0249387 A1 | 11/2006 | Willms et al. | |
| 2006/0273003 A1 * | 12/2006 | Sudo | B01D 63/081 210/498 |
| 2007/0269893 A1 | 11/2007 | Blankenstein et al. | |

FOREIGN PATENT DOCUMENTS

| | | |
|---|---|---|
| EP | 0239174 A1 | 9/1987 |
| EP | 1201304 A2 | 5/2002 |
| EP | 1495799 A2 | 1/2005 |
| EP | 1531003 A1 | 5/2005 |
| EP | 1559676 A2 | 8/2005 |
| EP | 1685900 A1 | 8/2006 |
| EP | 1714698 A2 | 10/2006 |
| JP | S56125663 A | 10/1981 |
| JP | S63502139 A | 8/1988 |
| JP | H06509424 A | 10/1994 |
| JP | 2001526391 A | 12/2001 |
| JP | 2001526778 A | 12/2001 |
| JP | 2002243748 A | 8/2002 |
| JP | 2005003688 A | 1/2005 |
| JP | 2005140790 A | 6/2005 |
| JP | 2005177754 A | 7/2005 |
| JP | 2005532151 A | 10/2005 |
| JP | 2006208388 A | 8/2006 |
| JP | 2006300944 A | 11/2006 |
| JP | 2007520692 A | 7/2007 |
| WO | 198706003 A1 | 10/1987 |
| WO | 199324231 A1 | 12/1993 |
| WO | 2001024931 A1 | 4/2001 |
| WO | 03103835 A1 | 12/2003 |
| WO | 2005119211 A1 | 12/2005 |

* cited by examiner

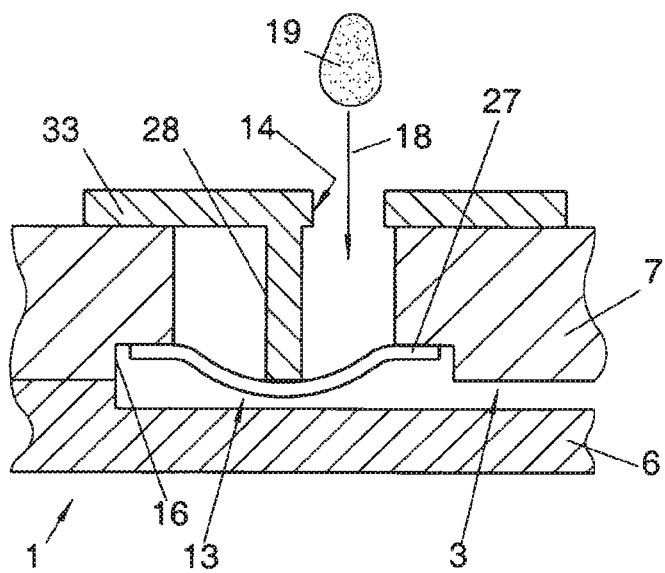
Fig. 14
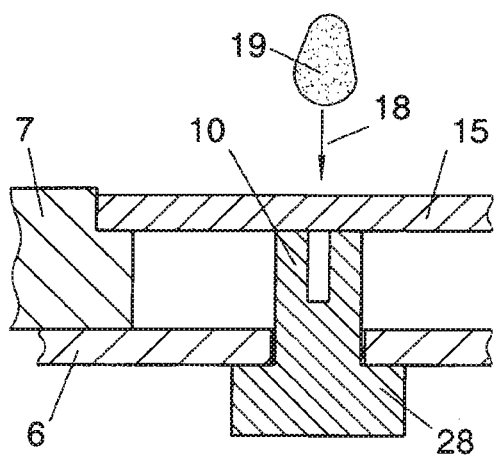
Fig. 15
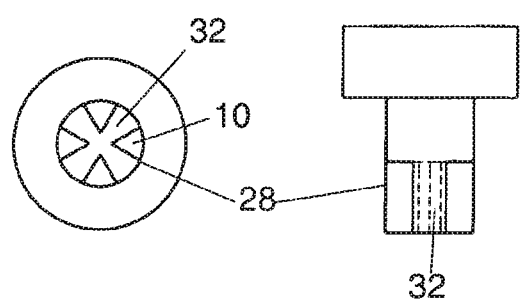

APPARATUS FOR THE SEPARATION OF PLASMA

The present invention relates to an apparatus for absorbing blood and separating blood components, e.g. blood plasma, as a sample liquid.

The present invention relates to microfluidic systems or apparatus. The following remarks apply to apparatus in which capillary forces act and are particularly crucial to the operation.

Apparatuses for separating blood plasma from blood are known from U.S. Pat. No. 4,906,439 A and WO 01/24931 A1 in each case, in which a plurality of groove-like or capillary-like individual channels are provided for receiving the blood plasma and carrying it away. The disadvantage here is that the channels fill up with the sample liquid in the form of blood plasma at different rates or not at all. Therefore a uniform liquid front cannot be achieved. This is problematic in terms of diagnostics as there is not a defined amount available at the same time or, for example, dry chemicals or the like cannot simultaneously be dissolved by the sample liquid in the desired or necessary amounts.

The aim of the present invention is to provide an improved apparatus and an improved process for absorbing blood and separating blood components, such as blood plasma, as a sample liquid, while permitting optimised filling of the channel with sample liquid and providing capillary contact between the separation element and the channel and preferably improving the diagnostic or investigative possibilities.

A fundamental idea of the present invention is to provide a device for creating fluidic capillary contact between separation elements, particularly membranes and a conveying channel. This allows optimal, rapid and uniform filling of the channel and prevents unwanted trapped air.

Preferably the sample liquid is absorbed by capillary forces in a channel which is open in construction at least on one narrow or longitudinal side, so as to form a lateral liquid stop for the sample liquid in the channel and to enable the sample liquid to be guided in the channel without any side walls. In particular a recess laterally adjoins the open side of the channel.

This ensures, by a simple method, that the sample liquid is prevented from being pushed forwards—i.e. the channel being filled more rapidly—in the region where a side wall would otherwise be provided. This allows the filling speed to be evened out over the entire cross-section of the channel, so that an at least substantially uniform or straight liquid front can be achieved during the filling of the channel.

The laterally open construction of the channel ensures an improved, particularly optimum venting when the channel is filled with sample liquid.

Moreover the surface of the sample liquid which is held or guided without any side walls enables the sample liquid to be examined directly, particularly by the focussing of light thereon, without a side wall or the like that would otherwise be provided.

Preferably the recess is of a trough-like construction and totally surrounds the channel which is open on all sides, in particular. Thus, especially with very fine structures, the inner edges that would normally occur at the transition from the flat sides to the narrow sides and that have particularly high capillary forces can be done away with completely. However, the same is also true when the channel is open at the sides only in parts.

Alternatively the recess or side wall laterally adjoining the channel may also be capable of being filled with sample liquid or some other liquid. The recess or side wall is then constructed—particularly with regard to its size, curvatures or wetting characteristics—or configured by means of deflector elements such that the fill speed of the channel with the sample liquid is greater than or equal to the fill speed of the recess or along the side wall in the direction of filling—particularly the longitudinal direction—of the channel. In this way, also, it is possible to prevent the liquid front from advancing laterally as it is filled with sample liquid.

Another proposed process for determining a parameter in the blood plasma or a blood component is characterised in that in a microfluidic system, immediately after blood cells have been held back or separated off, a component or parameter of the blood plasma is determined directly by means of one or more chemicals. This allows rapid and inexpensive analysis or determination of the parameter using an apparatus of simple and compact construction.

Figure 2:
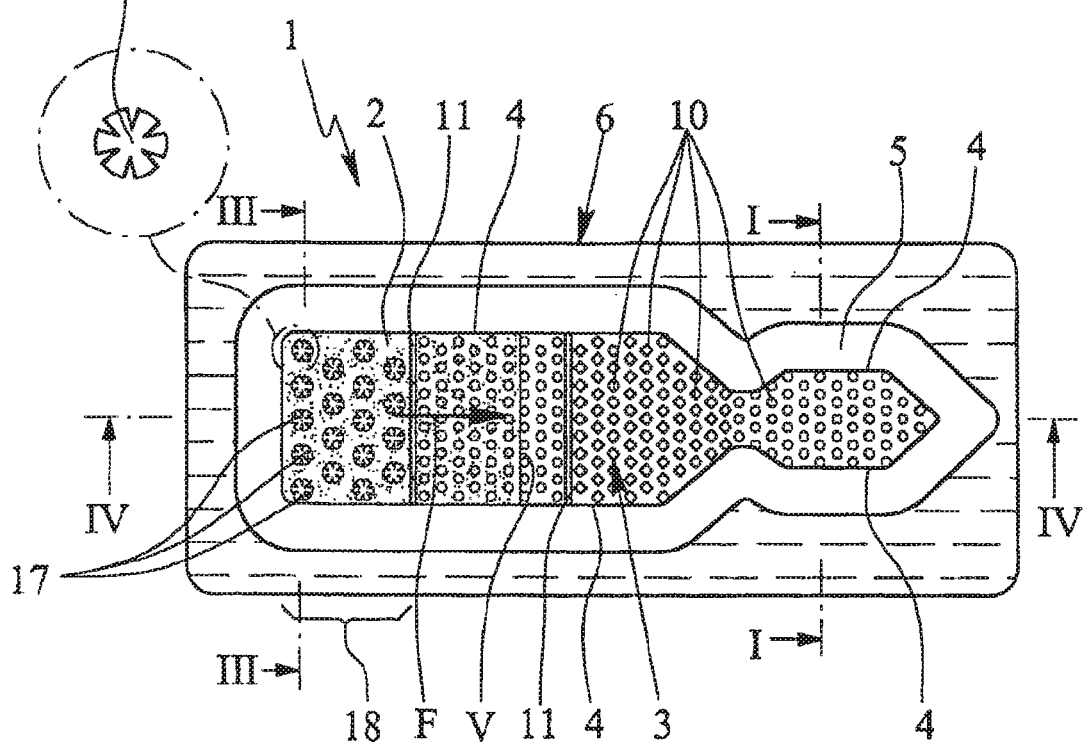
Figure 3:
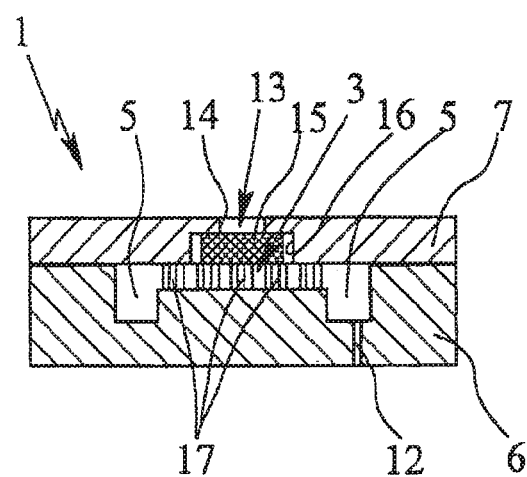
Figure 4:
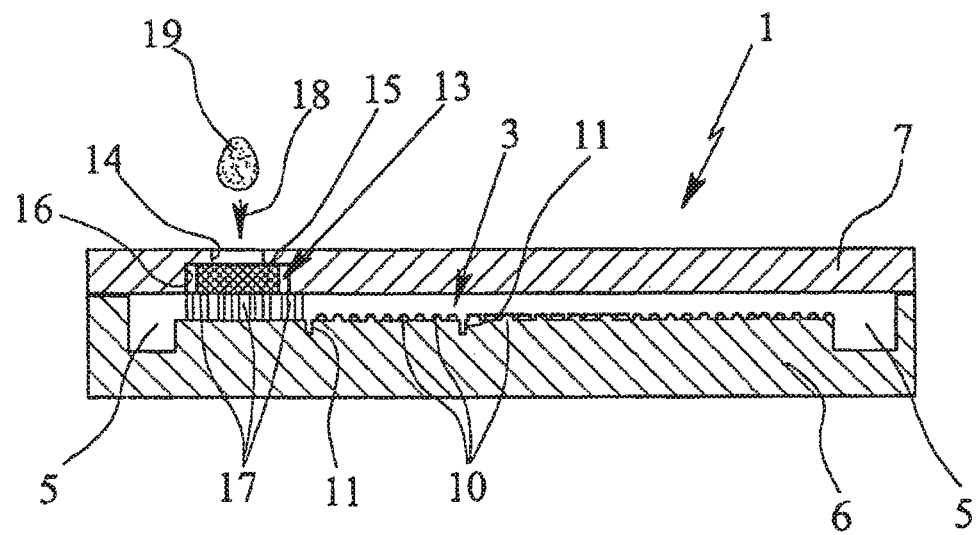
Figure 5:
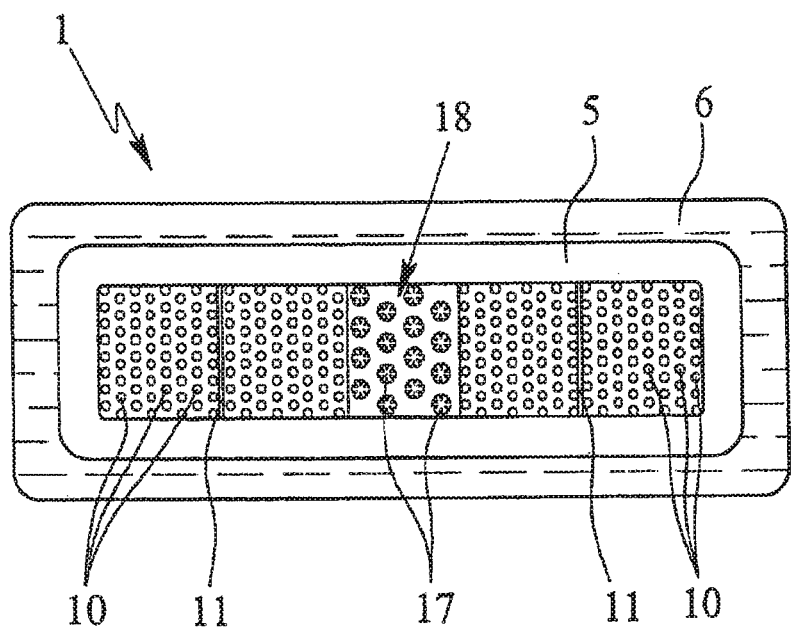
Figure 6:
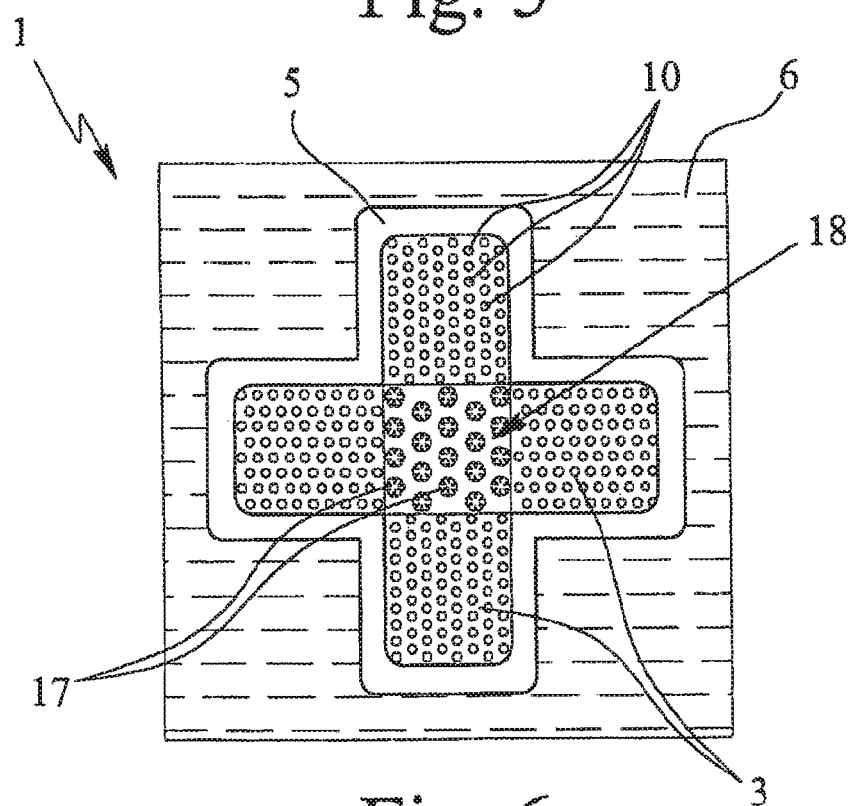
Figure 7:
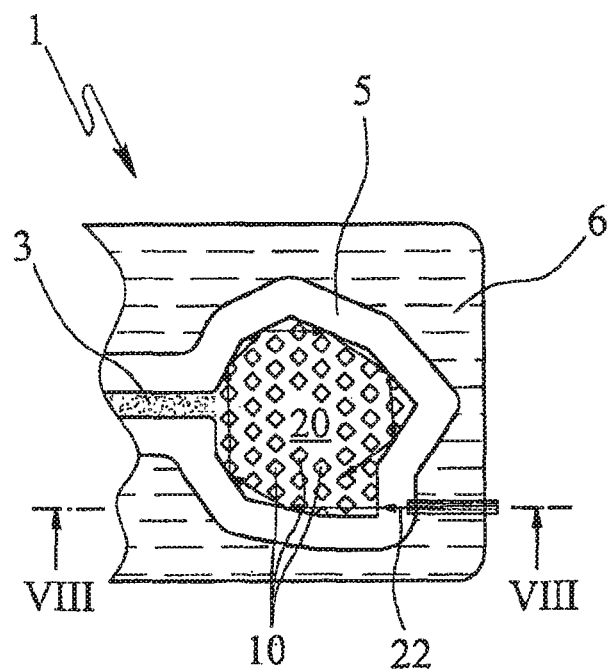
Figure 8:
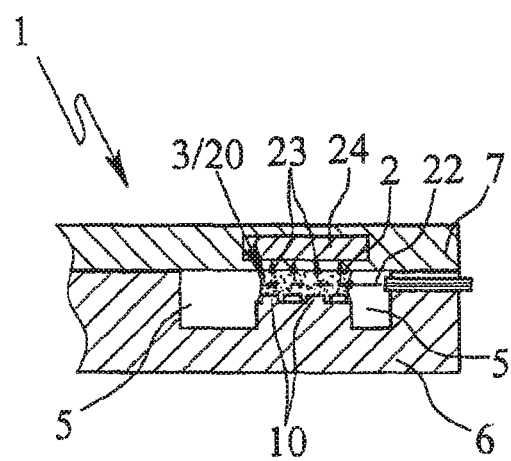
Figure 9:
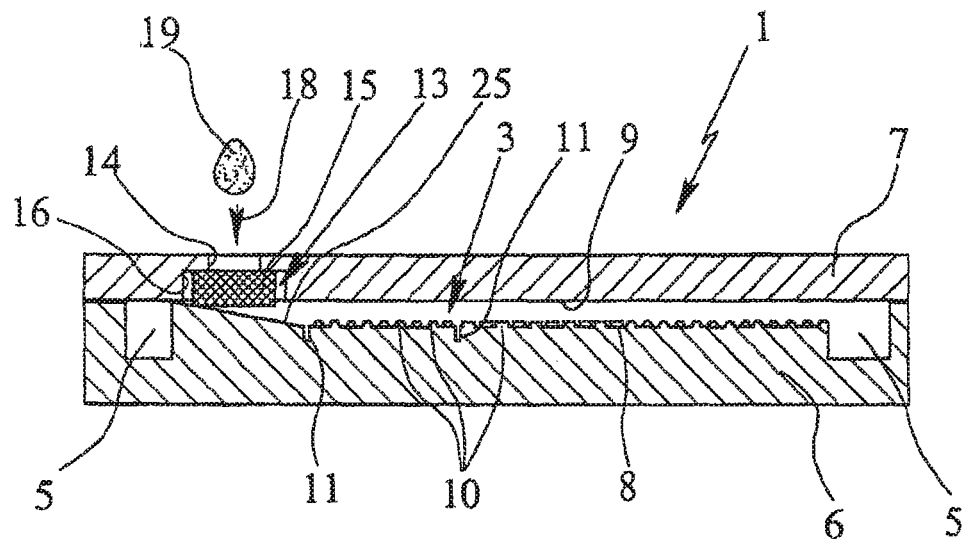
Figure 10:
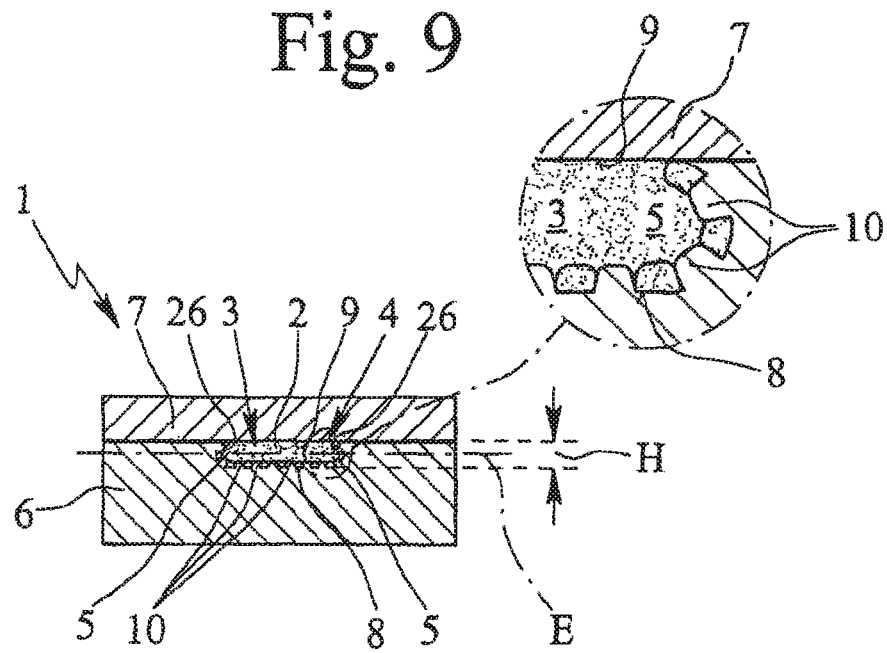
Figure 11A:
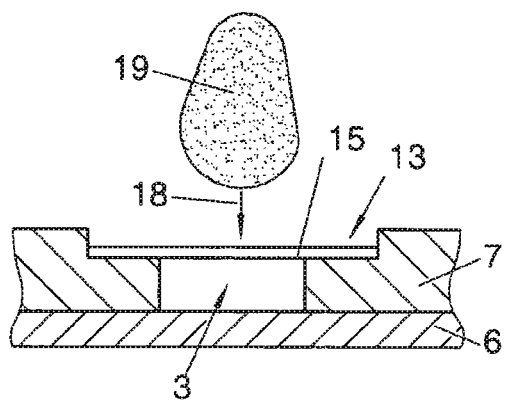
Figure 12:
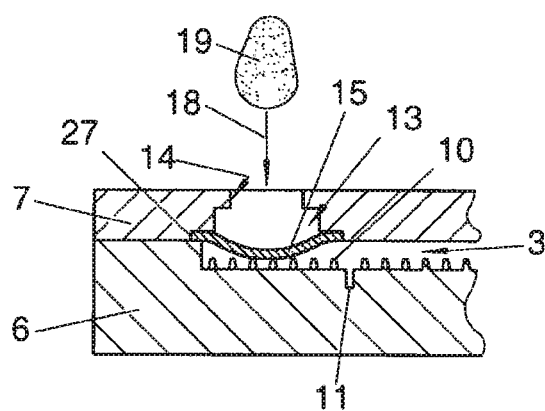
Figure 12A:
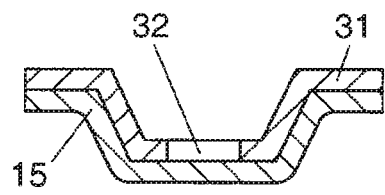
Figure 17:
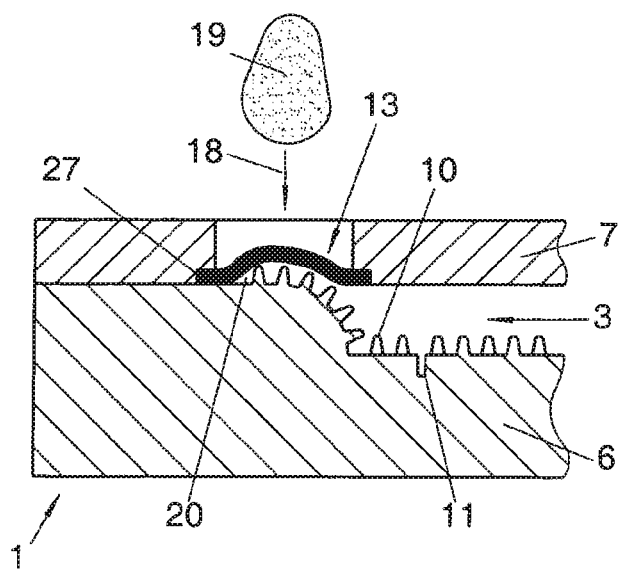
Figure 18:
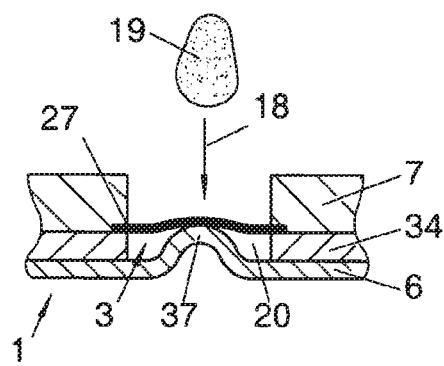
Figure 19:
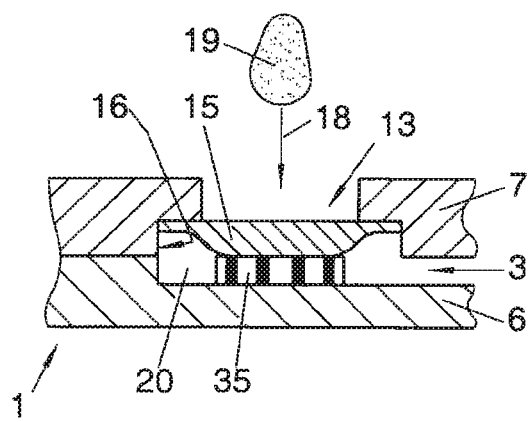
Figure 19A:
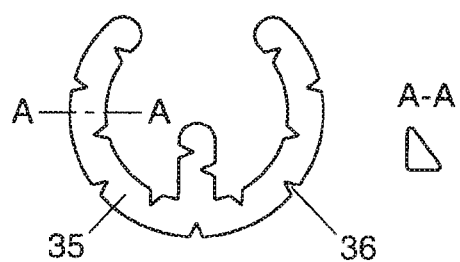
Figure 19B:
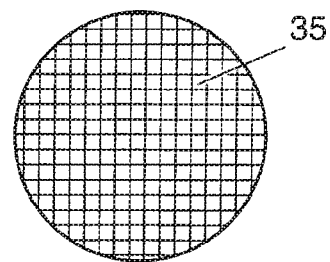
Figure 20:
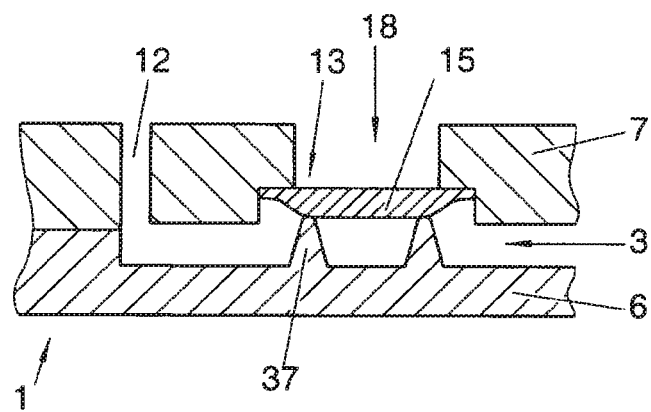
Figure 21:
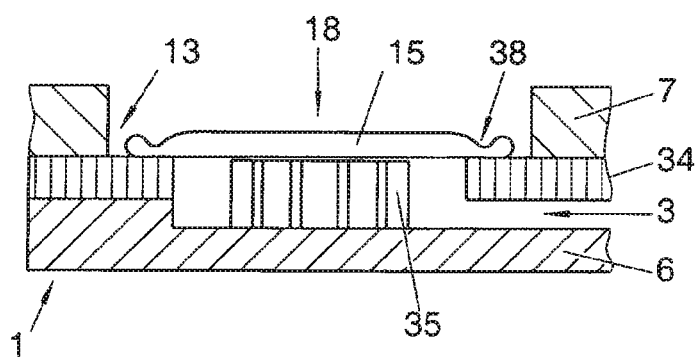

Further advantages, features, properties and aspects of the present invention will become apparent from the claims and the following description of preferred embodiments by reference to the drawings. These show:

FIG. 1 a schematic section through a proposed apparatus according to a first embodiment;

FIG. 2 a schematic plan view of a carrier of the filled apparatus according to FIG. 1;

FIG. 3 a schematic section through the apparatus on the line III-III according to FIG. 2;

FIG. 4 a schematic longitudinal section through the apparatus on the line IV-IV according to FIG. 2;

FIG. 5 a schematic plan view of a carrier of a proposed apparatus according to a second embodiment;

FIG. 6 a schematic plan view of a carrier of a proposed apparatus according to a third embodiment;

FIG. 7 a schematic plan view of a detail of a carrier of a proposed apparatus according to a fourth embodiment;

FIG. 8 a schematic section through a detail of the apparatus on the line VIII-VIII according to FIG. 7;

FIG. 9 a schematic longitudinal section through a proposed apparatus according to a fifth embodiment; and FIG. 10 a schematic section through a proposed apparatus according to a sixth embodiment;

FIG. 11A, B, C, FIGS. 12 and 12A an embodiment with a convex membrane arrangement;

FIG. 13A, 13B, FIG. 14, FIG. 15 and FIG. 16 embodiments with a membrane made convex by a punch;

FIG. 17 and FIG. 18 embodiments with convex carrier bases;

FIG. 19 and FIGS. 19A and 19B embodiments with an inlaid insert;

FIG. 20 an embodiment with a vent;

FIG. 21 an embodiment with a welded membrane and

Figure 22:
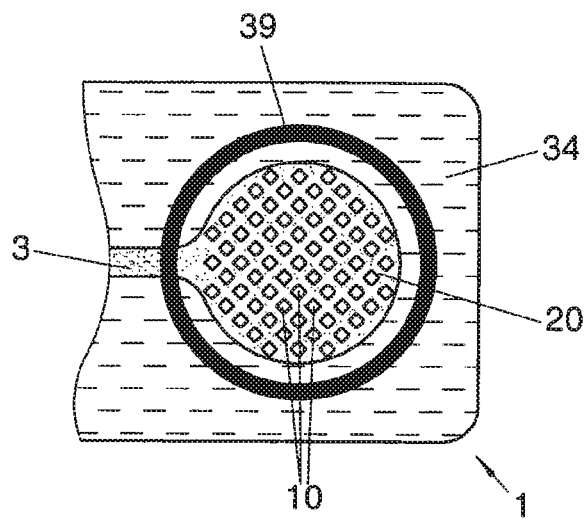
Figure 23:
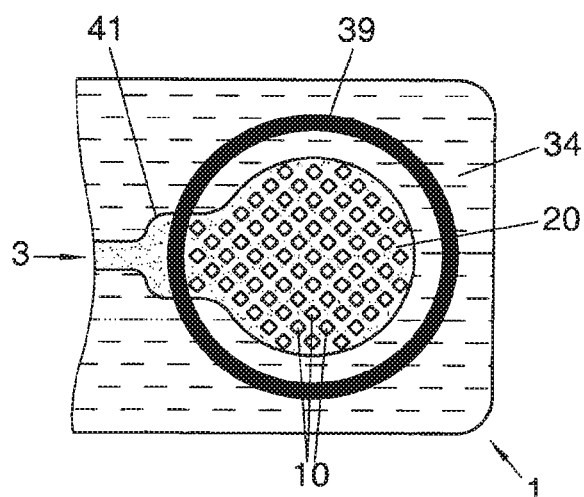
Figure 23A:
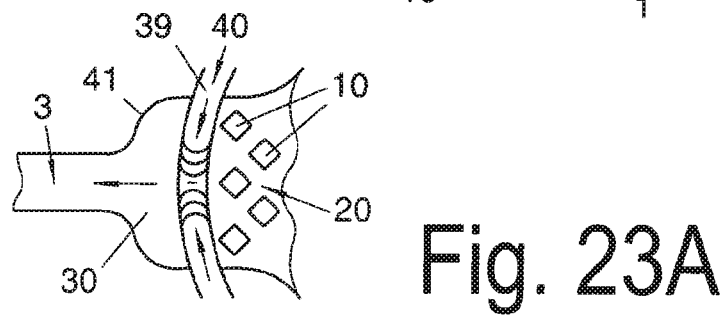

FIG. 22, FIG. 22 A, FIG. 23 and FIG. 23A a widening of the inlet cross-section of the channel.

In the figures the same reference numerals are used for identical or similar parts, while corresponding or comparable properties and advantages are achieved even if the relevant description is not repeated.

FIG. 1 shows in schematic section a first embodiment of a proposed apparatus (1) for absorbing and/or diagnosing a sample liquid (2), particularly blood plasma or the like. The apparatus (1) has a channel (3) which takes up the sample liquid (2) by means of capillary forces. The channel (3) is of open construction, at least on one narrow side or longitudinal side (4), on both narrow or longitudinal sides (4) in the embodiment shown, as indicated in FIG. 1.

Finally, adjoining the open sides (4) is a recess (5) which is preferably in the form of a groove or trough in the embodiment shown.

Thus, a lateral liquid stop for the sample liquid (2)—therefore an obstacle to flow that cannot be overcome by capillary forces—is formed in the channel (3) and the sample liquid (2) can be guided along the open sides (4) in the channel (3) without any side walls.

In the embodiment shown the apparatus (1) has a carrier (6) and an associated cover (7), between which are formed the channel (3) and the recess (5). If necessary, only the carrier (6) is cut away to form the necessary structures and the cover (7) is of even construction, preferably at least substantially free from recesses. However the situation may also be reversed. If necessary, however, both the carrier (6) and the cover (7) may be recessed and/or constructed with projections to form the desired structures and optionally designed to receive chemicals, reagents, investigation means or the like (not shown).

The recess (5) preferably adjoins the channel (3) with a sharp edge, as shown in FIG. 1. In the embodiment shown, the recess (5) is formed only in the carrier (6) and thus, in the view shown in FIG. 1 it extends substantially only downwards in relation to a lateral projection of the channel (3). The recess (5) may however extend upwards or on both sides of the lateral projection of the channel (3)—i.e. upwards and downwards, in particular, as desired.

The recess (5) which is preferably rectangular in cross-section leads to an increase in the cross-section of a kind, particularly stepwise or sudden, that causes the capillary forces to be reduced so that the above-mentioned liquid stop for the sample liquid (2) is formed in the transition from the channel (3) to the recess (5), as indicated in FIG. 1.

The channel (3) is preferably defined or formed by only two opposing, particularly substantially flat surfaces or flat sides (8) and (9), which are formed by the carrier (6) or the cover (7) in the embodiment shown and run parallel. If required, therefore, the recess (5) may be omitted altogether and the channel (3) be formed for example by two suitable strips or the like, at a suitable spacing for the production of the desired capillary forces.

FIG. 2 shows in schematic plan view the carrier (6) of the apparatus (1) without a cover (7), but partially filled with the sample liquid (2) up to the liquid front V. In the embodiment shown, the recess (5) extends along the open side(s) (4) of the channel (3), preferably at least along opposing open longitudinal sides (4). Moreover, in the embodiment shown the channel (3) is constructed to be laterally open on all sides and the recess (5) is accordingly of encircling design.

The channel (3) is thus surrounded by the recess (5) on all sides.

Preferably the recess (5) adjoins those narrow sides or longitudinal sides (4) of the channel (3) which extend at least substantially parallel to the main direction of filling F of the channel (3) with sample liquid (2), as indicated in FIG. 2. Consequently, the recess (5) preferably extends at least partially parallel to the main direction of filling F.

According to another alternative embodiment which will be described hereinafter with reference to FIG. 10 it is also possible for the recess (5) to fill up with the sample liquid (2) or with another liquid that is immiscible with the sample liquid (2), in particular, such as oil or the like. In this case, however, the recess (5) is constructed so that its fill speed is at most as great as the fill speed of the channel (3), to allow it to be filled as uniformly as possible with sample liquid (2). The fill speeds each relate to the filling or advancing of the liquid front V in the main direction of filling F.

Alternatively the recess (5) may also be flushed only with the other liquid before the sample liquid (2) is introduced.

The channel (3) preferably comprises a substantially rectangular and/or flat cross-section, particularly at right-angles to the main direction of filling F.

The height H of the channel (3) indicated in FIG. 1—i.e. the spacing of the preferably parallel surfaces (8) and (9) that delimit the channel (3)—is at most 2000 microns, preferably at most 500 microns, particularly about 50 to 200 microns. The recess (5) preferably leads to a stepwise or sudden increase in the height H and hence to the formation of the desired liquid stop. In particular, the height H of the recess (5) is at least twice as great as the height H of the channel (3).

The width B of the channel (3) is preferably about 100 to 5000 microns, particularly about 200 to 4000 microns.

The height H of the channel (3) is substantially less, particularly by at least a factor of 5 or 10, than the width B of the channel (3).

The capacity of the channel (3) is preferably less than 1 ml, particularly less than 100 µl, particularly preferably not more than 10 µl.

The apparatus (1) thus forms a microfluidic system. In particular, the apparatus (1) serves for microfluidic diagnosis for medical or non-medical or other investigations.

The channel (3) and hence its main direction of filling F and main extension plane E preferably extend at least substantially horizontally in the position of use. Depending on the intended use or design solution, however, a different alignment is also possible, particularly as the uptake or filling of the channel (3) with sample liquid (2) is preferably determined or carried out primarily by capillary forces alone.

Thus, the main direction of filling F may extend horizontally or at an angle, while the main extension plane E extends vertically, for example, so that the channel (3) is therefore aligned on edge.

The channel (3) preferably forms at least one reservoir for the sample liquid (2), particularly for diagnostic purposes. The channel (3) may optionally contain a chemical (not shown), particularly a dry chemical or the like. However, investigations on the sample liquid (2) may also be carried out in some other way.

In the embodiment shown, the channel (3) comprises at least one deflector element for influencing and particularly evening out the filling thereof with the sample liquid (2). According to an alternative embodiment, the channel (3) preferably comprises regularly distributed elevations (10) as deflector elements. These are arranged particularly in rows, at right angles, preferably perpendicularly, or longitudinally with respect to the main direction of filling F, particularly alternately offset at right angles. The elevations (10) are the rows offset in the main direction of filling F. In this way the sample liquid (2) can be made to fill the channel (3) row by row, and as a result advance with a substantially straight liquid front V in the main direction of filling F.

If necessary, the surface density, the spacing and/or the size of the elevations (10) may vary, particularly as a function of their respective distances from an inlet for the sample liquid (2) into the channel (3), not shown in FIGS. 1 and 2.

The elevations (10) are preferably in the form of webs, humps or columns, particularly with a round or polygonal base surface. However, it would also be possible to provide depressions instead.

Alternatively or additionally the channel (3) may comprise at least one trough (11) or a web as the deflector element extending transversely or longitudinally with respect to the main direction of filling F of the channel (3). The groove-like trough (11) which is preferably provided and which is in particular rectangular or semi-circular in cross-section has a substantially lesser depth than the recess (5) and therefore forms a purely temporary liquid stop for evening out the liquid front V. In this way it can be ensured that the sample liquid (2) does not fill the trough (11) and then the subsequent channel region until after it has filled the channel (3) over its entire cross-section.

It should be emphasised that by combining the guidance of the sample liquid (2) and deflector elements without the use of side walls it is possible to achieve a highly uniform filling of the channel (3) by capillary forces with a liquid front V which extends at least substantially in a straight line or perpendicular to the main directional filling F.

Alternatively, the channel (3) and/or a reservoir, collecting chamber, collecting region or the like formed thereby may also be at least substantially smooth or flat in construction, i.e. without deflector elements, in particular.

FIG. 3 shows another schematic section through the apparatus (1) with the cover (7) along the line III-III in FIG. 2.

The apparatus (1) has at least one vent (12) associated with the channel (3), which is connected not directly to the channel (3) but to the recess (5). Thus there is no need for an additional liquid stop for the vent (12) to prevent the sample liquid (2) from escaping through the vent (12). The construction of the channel (3) which is preferably laterally open on all sides allows optimum venting while the channel (3) is filling with the sample liquid (2) so that unwanted air inclusions can be reliably prevented.

The sample liquid (2) can be conveyed to the channel (3) preferably perpendicularly to the channel extent E, particularly vertically, in the position of use.

The apparatus (1) has a feed device (13) for taking up and supplying sample liquid (2) to the channel (3). In the embodiment shown the feed device (13) comprises an opening, particularly a perforation (14) in the cover (7), preferably for receiving blood or the like, and a separating device (15) such as a filter, membrane or the like for separating off blood plasma as the sample liquid (2). The separating device (15) in the embodiment shown is inserted in a gap (16) in the cover (7) opening towards the carrier (6) and covers the perforation (14). Preferably the separating device (15) is fixedly connected to the cover (7), for example by welding or gluing or is held thereby by frictional or interlocking engagement. The separating device (15) is directly in contact with the channel (3), by means of a flat side in the embodiment shown, and in particular the separating device (15) lies on preferably column-shaped structures (17) or the like in the channel (3) in a feed region (18) of the channel (3). The structures (17) are preferably provided with wedge-shaped recesses or the like to deflect the blood plasma or sample liquid (2) by capillary forces to the channel surface opposite the separating device (15), in this instance to the base surface (8) of the channel (3) formed by the carrier (6), and thus ensure total filling between the base surface (8) and the cover (7) or of the feed region (18) with sample liquid (2).

The structures (17) form a filling device for (totally) filling the channel (3) between the cover (7) and base surface (8) with sample liquid (2). However, this filling device may also be constructed differently, as will be explained later on by means of the fifth embodiment.

Next the sample liquid (2)—after overcoming the first trough (11) in the embodiment shown—is sucked further into the channel (3) by capillary forces, as indicated by the main direction of filling F in FIG. 2.

FIG. 4 shows in schematic longitudinal section the preferred structure of the proposed apparatus (1) according to the first embodiment, in which a drop of blood (19) which has been supplied is shown for illustration purposes.

The separating device (15) may if necessary contain a chemical, particularly a dry chemical, particularly to allow the separation of blood plasma as the sample liquid (2) from the blood (19) as desired in the embodiment shown, or to assist this separation and/or if necessary to allow lysing of cells. The separation or further conveying take place particularly solely by capillary forces. Preferably, only a single channel (3) for receiving or conveying the sample liquid (2) adjoins the feed device (13). The channel (3) should be understood as being a single capillary. If necessary, however, the channel (3) may lead in different directions or to different areas or may branch, as will be explained hereinafter with reference to the second embodiment according to FIG. 5 and the third embodiment according to FIG. 6.

FIGS. 5 and 6 each show a plan view of the carrier (6) of the apparatus (1) according to the second or third embodiment, without a cover (7) in each case.

In the second embodiment shown in FIG. 5 the channel (3) extends, starting from the feed device (13) or the feed region (18), onto opposite sides or in opposite directions, for example in order to carry out different investigations, tests or the like simultaneously. This produces a substantially elongate arrangement.

In the third embodiment shown in FIG. 6 a cross-shaped configuration is provided. The channel (3) extends in four different directions. Thus, for example, four different investigations, tests, reactions or the like can be carried out simultaneously.

Both in the second embodiment and in the third embodiment the recess (5) is preferably again provided for at least partial guidance of the sample liquid (2) in the channel (3) without the use of side walls. In particular, the recess (5) surrounds the entire channel configuration completely, while the channel (3) may preferably be constructed so as to be laterally open on all sides.

FIGS. 7 and 8 show a fourth embodiment of the proposed apparatus (1) and specifically FIG. 7 shows a plan view of the carrier (6) without a cover (7) and FIG. 8 shows a sectional view along the line VIII-VIII in FIG. 7 with the cover (7) present. The channel (3) here forms a collecting chamber (20) for the sample liquid (2). The collecting chamber (20) is in turn substantially flat in construction and comprises, as necessary, the elevations (10) shown and/or other deflector elements or the like.

The apparatus (1) according to the fourth embodiment comprises a device (21), particularly an optical fibre or the like, for conducting light into the sample liquid (2), particularly for measuring fluorescence. The light strikes the free surface of the sample liquid (2) in the region of an open side (4) of the channel (3) and as a result of a correspondingly steep direction of impact which is preferably substantially perpendicular to the surface of the liquid, it enters the sample liquid (2) as indicated by the arrow (22). The gas (air)/sample liquid (2) interface is used for the entry of light. This avoids the need for the light having to be guided by a side wall, as would normally be present, and thus undesirably scattered or causing fluorescence.

As indicated in FIG. 7, the incident light beam (22) is preferably reflected many times by total reflection at the sample liquid (2)/gas (air) interface. This is achieved by making the angle between the surface perpendicular and the incident light beam greater than the critical angle of the total reflection. The ground or base surface of the collecting chamber (20) which is delimited and defined by the encircling recess (5) is designed accordingly in order to achieve the desired beam guidance and total reflection, by a suitable polygonal configuration in the embodiment shown. The light (22) radiated in is used for fluorescence determination or fluorescence spectroscopy. The sample liquid (2) particularly marker molecules or the like contained therein, which are present as chemicals in the channel (3) and dissolved by sample liquid, are excited by a particular wavelength. This leads to electron transitions in the molecules which revert to their original state after a certain length of time, emitting a photon. The radiation emitted is indicated by arrows (23) in FIG. 8 and can be detected by a detector (24). In order to exclude the influence of the elevations (10) or other deflector elements on the incident light beam (22), the plane of the light beam is arranged above these structures or at a spacing from them. Moreover, the light beam plane runs at least substantially parallel to the main extension plane or in the main extension plane E of the channel (3) or of the collecting chamber (20).

The light radiation and light guidance provided ensures substantially total excitation of the sample liquid (2) or of marker molecules or the like contained therein and at the same time allow the use of micro-structures such as the elevations (10) or similar deflector elements. Capturing the emitted light beams (23) at right angles, particularly perpendicularly, to the direction of incidence (22) is optimum with regard to disengagement from the incident light.

FIG. 9 shows a schematic longitudinal section through a fifth embodiment of the proposed apparatus (1).

Compared with the first embodiment, the filling device for filling the channel (3) comprises, between the two flat sides (8) and (9), particularly for deflecting the blood plasma or the sample liquid (2) from the separating device (15) or from the cover surface (9) to the opposing base surface (8) so as to form a spatial meniscus between the two surfaces or flat sides (8) and (9), a slope or ramp (25), alternatively or in addition to the structures (17), said slope or ramp (25) correspondingly reducing the channel height H or even allowing it to become zero. In particular, the separating device (15) may be in direct contact with the ramp (25) or may rest directly thereon. The filling device mentioned may also be referred to or understood as a device for wetting the cover and base.

The schematic sectional view shown in FIG. 10 shows a sixth embodiment of the proposed apparatus (1). Here, the recess (5) laterally adjoining the channel (3) can be filled by the sample liquid (2) and constructed, particularly on the basis of a corresponding rounding-off of its side wall (26) and/or by the formation of corresponding guide elements such as elevations (10) or the like, such that the fill speed of the recess (5) in the main direction of filling F—i.e. perpendicular to the plane of the drawing in the representation shown in FIG. 10—does not exceed the fill speed of the channel (3), so as to prevent unwanted lateral advancing of the liquid front. It should be noted that in the embodiment shown the height H of the recess (5) corresponds to only about the height H of the channel (3). However, it is preferably greater. The proposed apparatus (1) is suitable for all kinds of tests, investigations or the like. In particular, it allows immunological or biochemical testing, for example, of blood (19), blood plasma or the like.

According to one alternative embodiment the channel (3) may have a number of investigation regions or collecting regions (20) which can be filled with the test liquid (2) one after another. Thus, it is possible for example to carry out various investigations one after the other and/or to expose the sample liquid (2) successively to different reagents, particularly dry chemicals, which are dissolved one after another.

According to another alternative embodiment, a second investigation or collecting region (20) may adjoin a first investigation or collecting region (20), the second region preferably having a substantially greater capillarity, for example by the use of an inserted nonwoven fabric or the like. The sample liquid (2), after the first region has been filled and in particular after a dry chemical provided therein, as necessary, has been dissolved, can then be sucked or conveyed into the second region, the dry chemical being washed out of the first region and in this way, for example, a further investigation is made possible in the first and/or second region.

According to another alternative embodiment, a first chemical, particularly a dry chemical, is provided preferably in the feed device (13) or separating device (15), and at least one second chemical, particularly a dry chemical, is provided preferably in the channel (3) or collecting region (20). This allows effective handling or influencing of the sample liquid (2), blood (19) or the like. Preferably, in order to investigate blood plasma, the first chemical is designed to prevent or delay clotting of the blood (19). For this purposes, EDTA (Ethylene Dyamine Tetra-acytic Acid) can be used as the first chemical, for example, in order to produce EDTA blood. The EDTA binds the calcium in the blood which is necessary as Factor IV for blood clotting.

Then the second chemical, preferably a mixture of chemicals, is used for an investigation or to determine one or more parameters in the blood plasma, such as glucose, ketones or lactate.

Preferably, in order to investigate at least one intracellular parameter such as the haemoglobin value or the calcium value in the blood (19), the first chemical is designed to lyse cells such as blood cells and release calcium or the like. Lysine buffer is used for this purpose, for example.

Then the second chemical, preferably a mixture of chemicals, is used to investigate or determine the parameter, particularly the calcium content. One ingredient of the mixture, preferably the chelating agent 8-hydroxyquinoline, is used to eliminate magnesium ions from the reaction as these would interfere with the reaction. Another complexing agent, preferably O-cresolphthalein, forms a coloured complex with calcium under alkaline conditions.

The extinction of the colour complex is proportional to the calcium concentration at a wavelength of 570 nm. It is determined directly in the channel (3) or collecting region (20) or optionally after removal. However, other measurements or procedures are also possible. In particular, the extinction may also be used at different wavelength and/or for determining different complexes, parameters or the like. The same applies to other, preferably optical methods of measurement, such as fluorescence measurements or the like.

According to yet another alternative embodiment, a removal opening (not shown) is provided in the cover (7) and/or in the carrier (6), to allow the removal of sample liquid (2), particularly blood plasma or the like which has been separated off. The removal opening is preferably connected to an at least relatively large-capacity storage region (20) or the like of the channel (3), to provide a desired or sufficient removal volume.

As a rule, the spacing of the membrane surface from the channel base is equal to the height of the channel, as shown in FIG. 11A. The problem then arises that the separating element for the blood separation may constitute a fluidic barrier to the unimpeded flow of the plasma into the channel. This is caused by the fact that a membrane or a filter element is used as the separating element, the membrane or the filter element consisting of a woven fibre network or a porous material. The materials used may be artificial fibres combined or compressed into a fleece or porous ceramics as well as metal meshes. The filter material has as a result of the mesh structure film branched channels with a high capillary force, which cause fluidic components to be retained in the filter or membrane. The membrane has a pore size of 0.01 microns to 1.2 microns, particularly 0.2 to 0.6 microns. The membrane density is from 50 microns to 500 microns, preferably 120 μm to 180 μm. The porosity, i.e. the proportion of the volume of the membrane which is not constructed with material, is 40-90%, preferably 70 to 80%. The pore material used may be various materials such as nylon, particularly isotropically foamed nylon 60, with a pore volume of more than 70% and a pore size of 0.5 microns or also preferably hydrophilic polyvinyldifluoride with a pore size of 0.6 microns.

Figure 11B:
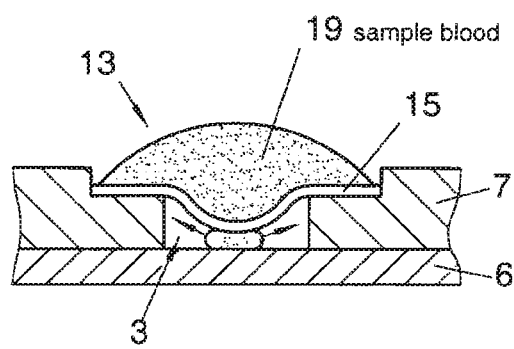

If a drop of blood is then placed in the entry region in the feed device (18), a hemispherical drop of blood forms on the surface of the membrane (15) as can be seen in FIG. 11b. As a result of gravity and fluid pressure, the blood plasma flows through the channels of the membrane (15), holding back the larger blood particles, and forms, as a result of the hydraulic pressure, a plasma film or plasma drop on the underside which adheres to the membrane. Because of the small amounts of blood or plasma or, in particular, when there is a large dead space to be filled between the membrane and the base of the channel, there may be no fluidic adhesion between the plasma and the channel. Admittedly, a plasma stream often flows along the channel walls to the channel base, in particular, and slowly fills the channel (3) or the collecting region (20). However, the start of the filling process is delayed by this, resulting in undesirably long flow times which have a negative effect on the function of a diagnostic or analytical apparatus connected to the fluidic channel structure. The dead space in the filling region between the separating element and the channel thus acts as an impedance or a resistance for the flow rate of the plasma.

A further aim of the present invention is to set this impedance to a controlled level, particularly to reduce it to a minimum.

Advantageously, the flow resistance can be minimised by constructing the separating element (15) as shown in FIG. 11B. For this, the separating element (15) is made convex in the direction of the channel base, so that it preferably rests on the channel base in a central region or alternatively the apex of the convex shape extends to close to the channel base. The spacing of the separating element from the bottom of the filling device, particularly from the channel base, is preferably from 1 micron to 100 microns, particularly from 10 microns to 25 microns.

Figure 11C:
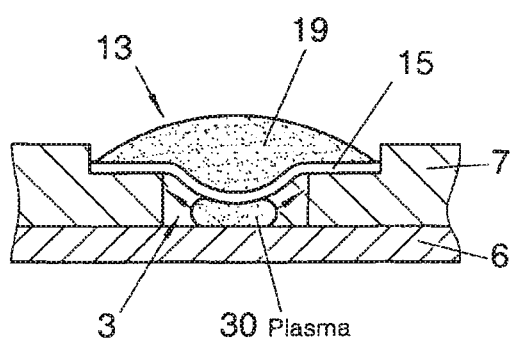

This ensures that the plasma liquid emerging from the underside of the membrane as a result of gravity or hydraulic pressure wets the channel directly and starting from this wetting point flows into the channel, as schematically shown in FIGS. 11B and 11C.

In a preferred embodiment the diameter of the membrane (15) used is from 2 to 10 mm, particularly 250 to 350 microns.

Advantageously, the height value W of the convexity or apex, as schematically shown in FIG. 12a, is in the region of the membrane density. In the Example shown previously, with a membrane thickness of 250 microns, the value W is preferably from 100 microns to 300 microns. The height value of the convexity should advantageously correspond roughly to the height of a channel in the inlet region or of a chamber located underneath the conveying membrane (15). As the depth of the channel constructed according to FIG. 1 is preferably 50-200 microns, the height W of the convexity may also vary in the range from 50 to 200 microns, according to the depth of the trough.

Advantageously, the channel walls and particularly the channel base comprise elements (10) that increase the volume flow in capillary manner as shown in FIG. 2. Particularly advantageously, an element (17) with vertical nodges is inserted on the channel base, as disclosed in AP 101 3341 B1. The geometry of the notch initiates and assists a vertical flow from the filling region through the separating element to the channel base.

FIG. 12 shows elements of this kind on the channel base, while a plurality of elements are arranged relative to one another on the base of the channel such that, as a result of the capillary winding of the interstices, there is a horizontal volume flow of the fluid or plasma in a collecting chamber (20) in the direction of the channel.

Advantageously, the convex curvature of the membrane is obtained by upsetting the membrane as it is secured in the direction of its centre, so that it is flexed through to the centre. This can also be achieved by making the diameter of the membrane greater than the diameter of the space in which the membrane is secured, particularly glued. With a corresponding retaining tool (not shown) that has a convex surface shape, the membrane is placed and glued in the fixing region. The convex shape of the tool causes the deflection of the membrane to be formed.

As an alternative to gluing, thermal processes such a welding, particularly ultra-sound welding, can be used for fixing the membrane, while the membrane is advantageously pressed in between two plastic elements of the apparatus with a pre-shaped retaining tool in this case as well.

As an alternative to shaping the separating element of the membrane during the fixing process, the convex deflection of the separating element can also take place beforehand by stamping the shape into the separating element.

With metal filter elements it is possible, for example, to press or bend them into a domed, particularly convex shape.

In the case of non-woven materials, a pressing operation in a correspondingly shaped tool with the application of pressure and/or temperature and/or additional chemical fixing agents or adhesives would also be possible. Alternatively, even during the manufacture of the nonwoven material from synthetic fibres, a convex shape might advantageously be impressed during the needling and consolidation of the nonwoven fabric.

In another advantageous embodiment the separating element is in two or more parts, particularly in two layers, while a flexible membrane is provided on a fixed holding element, particularly a membrane holder (31), as shown in FIG. 12A. Advantageously, the membrane is glued in the outer region of the funnel-shaped retaining element, but may also be secured by clamping elements. The funnel-shaped membrane holder or shaping insert (29) has a through-opening or bore (32) in a central region, so that when the funnel is filled with blood the latter can pass through the opening (32) into the membrane.

Figure 13A:
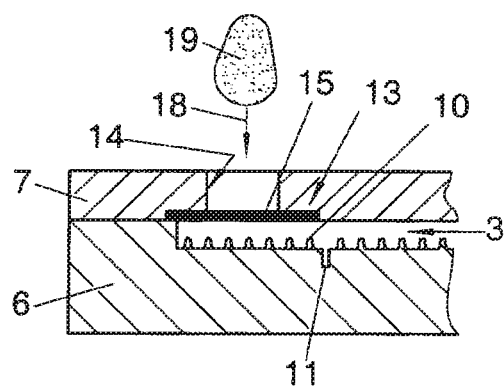

In another advantageous embodiment of the invention according to FIG. 13, a membrane (15) is provided as a separating device (15). When a drop of blood (19) is added to the feed region (18) and the opening (14) of the cover (6), the drop comes to rest on the membrane (15) which is flat in FIG. 13A.

Figure 13B:
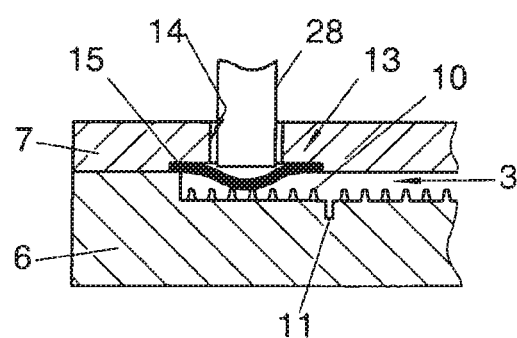

In the following step, as can be seen from FIG. 13B, a ram (28) is inserted in the opening (14), this ram deforming the membrane surface towards the interior of the channel, so as to produce a convex membrane shape.

The punch (28) is preferably also domed at its end which comes into contact with the membrane.

The insertion of the ram (28) may be done both manually by an operator or using an automatic operating device with actuating drive means. In the latter case the ram (28) is mounted on a positioning drive, the positioning drive moving the ram such that it presses the membrane downwards towards the base of the channel. The positioning drive can be operated by piezo-electrical positioning members or a stepping motor or other suitable mechanical or electrical actuating means. Preferably, the ram (28) is moved downwards as a function of the analysis step that is to be carried out.

On the apparatus, sensors may be provided for automatic movement of the ram (28). These sensors detect the feeding in of a drop of blood (19) and actuate the ram or punch (28) by means of a control device, especially a microprocessor which records and processes the sensor signals.

In another embodiment of the invention according to FIG. 14, the channel (3) is formed by a recess (5) in the carrier (6) and a congruent cut-out in the cover (7). The cover (7) has an opening in the end region of the channel (3). This opening (14) is closed off towards the top of the cover (7) by a pressure element (33).

The cover element (33) comprises a punch (28) and an opening (14) through which a drop of blood (19) can be fed into the feed region (18). In the cut-out (16) of the cover is provided a separating element (15), particularly a filter membrane, which is secured therein.

This securing may be done for example by means of gluing or welding to the cover (7). In the manufacture of the apparatus (1) according to FIG. 14, in a first step the membrane is attached to the cover (7). In a subsequent manufacturing step the cover (7) provided with the membrane and the carrier (6) are joined together.

In another manufacturing step following the first step, the covering element (33) is attached to the cover (7) as a result of which the ram (28) convexly deforms the membrane so that the dead space in the feed device (13) is reduced and the apex of the convex membrane (27) extends close to the base of the channel. This results in an apparatus (1) in which there is a significantly reduced fluid resistance between the membrane (27) and the channel (3).

In one embodiment of the invention according to FIG. 15, the punch (28) is inserted in a bore in the carrier (6) in the feed region. For this, the shaft of the punch has a first section adjoining the head of the punch, which corresponds in length to the thickness of the carrier (6) in the region of the bore and seals off the bore when the punch is inserted.

A second portion of the shaft of the punch is provided with notches or profiling or has perforations running through the longitudinal direction of the shaft. This second section of the shaft of the punch extends from the base of the feed region (18), particularly the base of the channel (3) or the base of a collecting chamber (20), up to the separating element (15) and is in contact with the latter, so that the profiled shaft of the punch establishes a vertical fluid connection between the base and a membrane (15).

Particularly advantageously, the shaft of the punch may be provided with elevations or deflector elements (10) on its preferably cylindrical outer surface, which assists capillary flow of the plasma that is separated off.

Figure 16:
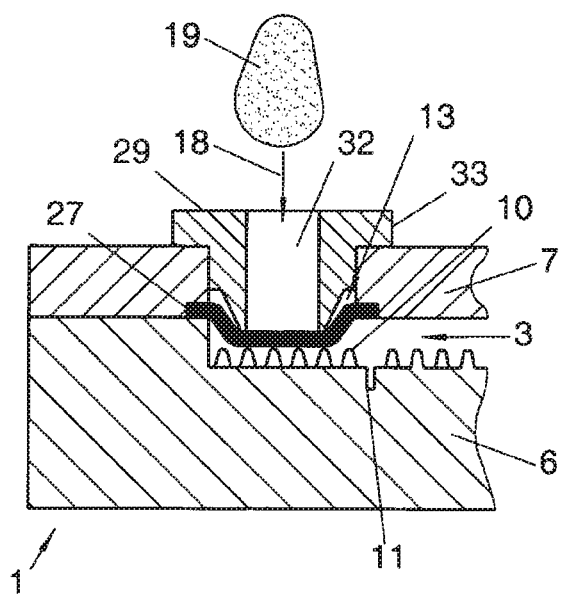

FIG. 16 shows an apparatus in which the cover element (33) is provided with a central bore (32) through which a drop of blood (19) is introduced into the feed region (18).

The cover element (33) is attached to the cover (7), for example ultra-sonically welded thereto.

The pressure element (33), cover (7) and carrier (6) are preferably made of plastics.

The membrane (27) is clamped between the cover (7) and the carrier (6), particularly welded in position.

In the embodiment according to FIG. 16, the pressure element (33) is in the form of a shaping insert (29), the shaping insert (29) being of 3-dimensional construction in the direction of the channel (3) such that the membrane is convexly curved and comes into fluidic contact with the base of the channel (3) particularly with the deflector element (10) on the base of the channel.

In an embodiment according to FIG. 17, during the manufacture of the apparatus (1), the separating element (15) is first connected to the cover (7) and closes off the feed region (18) of the feed device (13) downwards towards the entry region of the channel.

The carrier element (6) which has a cut-out in the form of a channel (3), is designed, in the region of the opening of the cover (7) i.e. in the region of the membrane (27) mounted flatly on the cover (7), such that in a region of the carrier (6) arranged opposite the central region of the opening the surface of the carrier extends beyond the junction plane between the carrier (6) and cover (7). This can be achieved, for example, by having the surface of the carrier (6) bulging convexly inwards into this region, as shown in FIG. 7, pressing against the membrane (27) and deflecting it accordingly to match the shape of the carrier (6). Advantageously the carrier surface is also provided in this region with deflector elements (10) which ensure that the plasma has a horizontal fluid flow.

In the embodiment according to FIG. 18 the apparatus (1) is constructed in three layers. The carrier (6) is connected to the cover via an intermediate element (34), in this case the channel element (34) that forms the channel. For this purpose the intermediate element (34) is glued to the carrier (6) and to the cover (7), for example. The intermediate element (34) is preferably a double-sided adhesive film. The channel structures, particularly the channel (3), are formed as cut-outs (16) in the intermediate element, for example by standing out of the finished shape or as cut-outs during the moulding or casting process.

Advantageously, in this embodiment in which all the guide channels and fluid chambers are arranged in the intermediate element, the cover (7) and the carrier (6) may be constructed as planar elements without recesses (5) for the fluid-conveying structures, thus considerably reducing the use of precise, high-cost micro-forming tools and making manufacture easier.

In the embodiment according to FIG. 18, in order to establish fluidic contact and reduce the flow resistance in the inlet region of the channel, the carrier element (6) is to be shaped in the direction of the membrane (27), particularly at least one peg (37) is to be inserted in the carrier element (6), this peg projecting from the junction plane between the channel element (34) and the carrier element (6) towards the membrane and providing fluidic contact with the membrane.

The peg (37) may for example be introduced directly into the carrier element during the manufacture of the carrier (6) by moulding or subsequently by mechanical and/or thermal embossing.

In an embodiment shown in FIG. 19 the channel (3) is formed as a recess (5) in the carriers (6).

The separating device (15), in this case a filter element (15), is arranged in a recess (16) and forms, together with the inlayed element or insert (35), the tensile dyed device (13). If a drop (19) of blood is fed into the feed region (18), the blood is absorbed and filtered by the filter (15), and the plasma emerging in the direction of the channel is taken up by the insert (35) arranged on the channel side of the filter (15).

The insert (35) is geometrically designed so that its height corresponds substantially to the height of the gap between the channel base and the underside of the filter (15) and the insert (35) makes contact both with the channel base or chamber base in the inlet region and also with the underside of the filter. Preferably, the insert (35) is an inlayed element (35) which means that when the carrier (6) is connected to the cover (7) the insert (35) is secured by being held by the contact pressure between the filter and the carrier (6).

The insert may be produced for example as an O-ring from an elastic plastics material or from rubber.

In a preferred embodiment of the insert (35) according to FIG. 19B the latter consists of another filter material which may be a porous ceramic material, a sponge made of fibre material, a metal grid or mesh element or some other suitable element made of structures which have channels.

Other materials that may be used are gel-like sponges or polymers such as polysaccherides or silicones. Examples of such polymers are sacarodes, polyaryamide or agarose. Advantageously, reagents such as anticoagulants (K2EDTA) may be introduced into the spongy or gel-like material.

In another preferred embodiment according to FIG. 19A the insert (35) is in the form of a horseshoe-shaped inlaid element (35). The inlaid element may consist of pore-free plastics material but it is also possible to produce the inlaid element from one of the above-mentioned channel-carrying materials.

Particularly preferably, the inlaid element has at least one notch (36) in its edge region, particularly a plurality of notches (36) which assist with vertical discharging of the plasma into the plasma chamber (20) of channel (3). Advantageously the cross-section of the inlaid parts may also be wedge-shaped, as shown by the section A-A in FIG. 19A, the apex of the wedge being in contact with the membrane surface and thereby establishing fluid contact.

The air present in the volume of the feed region may be included in the filling region when a drop of blood is added.

On the one hand this may have the effect of forcing air out of the region underneath the filter (15), which rests on the peg (37) according to FIG. 20 into the channel. These air bubbles present major flow resistance and are therefore undesirable. In addition there may be an accumulation of air which will build up a counter pressure to the hydraulic pressure of the plasma and constitute a serious flow impedance. Advantageously, therefore, a lateral vent (12) is provided in the collecting chamber (20) at right angles to the channel (3). A vent of this kind on the feed device (13) may be provided in all the embodiments according to FIGS. 1 to 23.

To ensure that the filter (15) is tightly sealed in a structure having a carrier (6), a cover (7) and an intermediate element (34), the filter is provided, in its fixing region, with a compression member (38) which compresses the filter material in the region of the compressing member (38). In an apparatus of this kind according to FIG. 21, a recess (5) is formed in a carrier element (6), to form the channel (3). The intermediate element is a plastic part in the form of a film provided with adhesive on both sides, the adhesive establishing contact by sticking both to the cover (7) and to the carrier (6) and attaching them to one another. Arranged in contact with the filter is an insert (35) in the form of an inlaid part (35) in the region of the feed device.

In an embodiment according to FIG. 18, the separating device or the filter (15) is glued or welded into the cover (7), welding being carried out for example by ultra-sound or by thermal welding.

In one embodiment of this arrangement according to FIG. 22 the feed region is shown from above. The plan view shows the intermediate element (34) which is, for example, a channel element with cut-outs which form a sample collecting chamber (20) in the feed region and a channel (3). Of the underlying carrier (6), the deflector elements (10) can be seen in the region of the sample chamber (20).

Above the plane of the intermediate element is schematically shown the weld line (fixing line) (39) which, lying in the upper cover (7), obstructs the filter or the filter membrane (15) with the cover. The intermediate element is, in particular, a film which is provided with an adhesive on both sides.

When a drop of blood is added, the plasma separated off flows into the collecting chamber (20) and is carried away into the channel (3) with the assistance of the deflector elements. The inlet region of the channel (3) constitutes a clear and abrupt reduction in the flow cross-section.

Figure 22A:
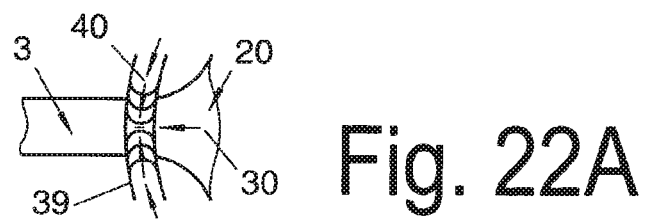

As shown in FIG. 22A, air may flow into the channel (3) as a result of which a stream of air bubbles may enter the channel, significantly increasing the flow resistance or bringing the flow to a complete standstill. In the region of the fixing line (39) in particular, there may be a transverse influx of air (40) as the filter material, as a result of the compression at this point during welding, leaves behind a cavity out of which air can flow inwards.

In an advantageous embodiment of the transition from the sample chamber (20) to the channel (3), it is therefore provided according to FIG. 23 that the cross-section of flow be reduced continuously from the collecting chamber to the channel along a transitional region. This may take place stepwise, for example, by reducing the cross-sectional area, as shown in FIG. 22, until the reduced cross-section (41) is about 2 to 5 times the cross-section of the channel (3).

As shown in FIG. 23A the cross-sectional step (41) is arranged so that the encircling fixing line (39) slows down the outlet region from the collecting chamber (20) in the region of the cross-sectional step and does not form a crossover to the channel (3), thereby preventing a direct influx of air (40) into the channel (3).

Admittedly, air flows into the region of the cross-sectional step (41) in this embodiment of the flow, but as it is has a larger cross-section it takes correspondingly longer for an influx of air bubbles to block this cross-section and possibly lead to a break-off of the fluid current.

In a number of the embodiments shown, the base of the channel (3) or the base of the feed device (18) comprises deflector elements (10). These deflector elements help to assist the wetting by a vertical flow of fluid. When suitably positioned relative to one another the interspaces with a capillary action between the deflector elements (10) also assist a horizontal flow of fluid.

One feature that is common to all these embodiments is that the deflector elements are not an essential operational component. The capillary gap present between a filter or a membrane (15) and the base of a channel (3) or a feed device (18) also acts in the same way as a deflector element (10), as the curvature of the base towards the membrane at the contact surfaces or feed surfaces result in wedge-shaped capillary gaps of low height and high capillarity.

The invention claimed is:

1. An apparatus (1) for absorbing blood (19) and separating blood components as a sample liquid (2), comprising:
    a carrier (6) defining a base of the apparatus and having a lower boundary surface,
    a feed device (13) spaced away from the lower boundary surface of the carrier (6) in a direction opposite to an input direction for receiving the blood (19) into the feed device (13),
    a separating device (15) for separating the blood components as the sample liquid (2), the separating device (15) being spaced away from the carrier (6) in the direction opposite to the input direction, the separating device (15) including a first surface facing the blood (19) as the blood (19) is received into the feed device (13) and a second surface opposite to the first surface and facing towards the lower boundary surface, where a volume is defined between the second surface of the separating device (15) and the lower boundary surface of the carrier (6),
    a channel (3), in fluid communication with the volume, which takes up the sample liquid (2) exclusively by capillary forces,
    a filling device for filling the channel (3) with the sample liquid (2) in an inlet or feed region (18) of the channel (3), and
    an insert (35) disposed in the volume between the second surface of the separating device (15) and the lower boundary surface of the carrier (6), where the insert (35): (i) is at least partially annular about an axis defined by the input direction, (ii) includes respective inner and outer cylindrical surfaces about the axis, and (iii) includes longitudinally disposed notches running on at least one of the inner and outer surfaces of the cylinder in directions parallel to the input direction of introducing the blood.

2. The apparatus according to claim 1, wherein the insert (35) is formed of at least one of a sponge, an O-ring, and an element carrying a porous channel.

3. The apparatus according to claim 1, wherein a height of the insert (35) corresponds approximately to distance between the second surface of the separating element (15) and the lower boundary surface of the carrier (6).

4. The apparatus according to claim 1, wherein the insert (35) is a substantially circular inlaid part.

5. The apparatus according to claim 1, wherein the insert (35) includes a mesh-like material.

* * * * *